United States Patent
Ryu et al.

(10) Patent No.: US 9,029,578 B2
(45) Date of Patent: May 12, 2015

(54) METHOD FOR PREPARATION OF ANHYDROSUGAR ALCOHOLS

(75) Inventors: Hoon Ryu, Daejeon (KR); Young Jae Jung, Seoul (KR); Young Seok Kim, Daejeon (KR)

(73) Assignee: Samyang Genex Corporation, Seoul (KR)

( * ) Notice: Subject to any disclaimer, the term of this patent is extended or adjusted under 35 U.S.C. 154(b) by 0 days.

(21) Appl. No.: 14/122,512

(22) PCT Filed: Jun. 2, 2011

(86) PCT No.: PCT/KR2011/004036
§ 371 (c)(1),
(2), (4) Date: Nov. 26, 2013

(87) PCT Pub. No.: WO2012/165676
PCT Pub. Date: Dec. 6, 2012

(65) Prior Publication Data
US 2014/0088315 A1    Mar. 27, 2014

(51) Int. Cl.
*C07D 493/04*    (2006.01)
*C07B 63/00*    (2006.01)
*C08G 63/672*    (2006.01)

(52) U.S. Cl.
CPC ............ *C07D 493/04* (2013.01); *C07B 63/00* (2013.01); *C08G 63/672* (2013.01)

(58) Field of Classification Search
CPC ..... C07D 493/04; C08G 63/672; C07B 63/00
USPC ........................................................ 549/464
See application file for complete search history.

(56) References Cited

U.S. PATENT DOCUMENTS

| 4,695,411 | A | * | 9/1987 | Stern et al. ................. 554/167 |
| 4,861,513 | A | | 8/1989 | Lueders et al. |
| 6,407,266 | B2 | | 6/2002 | Bhatia |
| 6,639,067 | B1 | * | 10/2003 | Brinegar et al. ............. 536/126 |
| 7,122,661 | B2 | | 10/2006 | Fleche et al. |
| 7,615,652 | B2 | * | 11/2009 | Holladay et al. ............. 549/464 |

FOREIGN PATENT DOCUMENTS

JP    2011-516574 A    5/2011
WO    WO 2009/126852 A1    10/2009

OTHER PUBLICATIONS

International Search Report issued in PCT/KR2011/004036, dated Feb. 16, 2012.
Fleche, G. et al, "Isosorbide—Preparation, Properties and Chemistry," Starch/Starke, 1986, vol. 38, pp. 26-30.

* cited by examiner

*Primary Examiner* — Noble Jarrell
*Assistant Examiner* — John Mauro
(74) *Attorney, Agent, or Firm* — Birch, Stewart, Kolasch & Birch, LLP

(57) ABSTRACT

A method is provided for the preparation of anhydrosugar alcohols. The method involves dehydration of a hexitol with a mixed acid of a first acid and second acid, in which the first acid is sulfuric acid and the second acid is at least one sulfur-containing acid or sulfur-containing acid salt selected from the group consisting of p-toluenesulfonic acid, methanesulfonic acid, ethanesulfonic acid, benzenesulfonic acid, naphthalenesulfonic acid and aluminum sulfate. Also provided are methods for purification of the resulting product.

15 Claims, No Drawings

METHOD FOR PREPARATION OF ANHYDROSUGAR ALCOHOLS

TECHNICAL FIELD

The present invention relates to a method for the preparation of an anhydrosugar alcohol in the form of a diol from hexitol. More specifically, the present invention relates to a method for the preparation for an anhydrosugar alcohol which includes dehydration of hexitol with a mixed acid of first acid and second acid.

BACKGROUND ART

Sugar alcohol collectively refers to compounds obtained by adding hydrogen atom(s) to a reducing end-group of saccharide, and generally have a chemical formula of $HOCH_2(CHOH)_nCH_2OH$ wherein n is an integer of 2 to 5 and is classified into tetritol, pentitol, hexitol and heptitol depending on the number of carbon atoms (4, 5, 6 and 7). Among these, hexitol containing 6 carbon atoms includes sorbitol, mannitol, iditol, and the like. In particular, sorbitol and mannitol are highly useful substances.

As a method for the preparation of an anhydrosugar alcohol using hexitol, there is known a method which includes dehydration of hexitol with an inorganic acid such as sulfuric acid or hydrochloric acid (Starch/Starke vol. 38. pp26-30). Further, dehydration of hexitol may also be carried out using cation exchange resins, zeolites, etc. Inorganic acids such as hydrochloric acid or sulfuric acid are relatively inexpensive and are capable of enabling easy preparation of anhydrosugar alcohol, but have a problem of low purification yields due to the production of large amounts of polymer by-products. On the other hand, cation exchange resins or zeolites are expensive and have problems of high recovery cost and a low conversion rate of hexitol into anhydrosugar alcohol.

Anhydrosugar alcohol is known to have a property of increasing a glass transition temperature of polymers such as polyesters. Further, it is known that anhydrosugar alcohol derivatives are beneficial for cardiac and vascular diseases, can be used in adhesives for patches, drugs such as mouthwashes, cosmetic compositions, etc., and can also be used as raw materials for environmentally-friendly plasticizers and environmentally-friendly solvents as well as raw materials for polyesters, polyurethanes, epoxy resins or the like in the chemical industry. In particular, great attention has focused on industrial applications such as polyesters, plasticizers or the like using anhydrosugar alcohol, but industrial utilization of anhydrosugar alcohol is still in-significant. This is believed to be due to limitations associated with high costs of catalysts used in dehydration reactions, low conversion rates and purification yields and the like associated with conventional methods for the preparation of an anhydrosugar alcohol.

Accordingly, there is an urgent need for a method for the preparation of an anhydrosugar alcohol which is capable of achieving high conversion rate and purification yield in conjunction with reduction of production costs.

DISCLOSURE OF INVENTION

Technical Problem

As a result of continuous research to solve the above-described problems of the conventional art and develop an industrially applicable method for the preparation of an anhydrosugar alcohol, the inventors of the present invention have discovered that the use of a mixed acid of first acid (sulfuric acid) and second acid containing sulfur (sulfur-containing acid salt) enables the production of anhydrosugar alcohol at low cost and with high conversion rate and purification yield upon carrying out dehydration of hexitol. The present invention has been completed based on these findings.

Therefore, it is an object of the present invention to provide an economical method for the preparation of an anhydrosugar alcohol with high conversion rate and purification yield.

Solution to Problem

In accordance with an aspect of the present invention, the above and other objects can be accomplished by the provision of a method for the preparation of an anhydrosugar alcohol, including dehydrating hexitol with a mixed acid of first acid and second acid, wherein the first acid is sulfuric acid, and the second acid is at least one sulfur-containing acid (sulfur-containing acid salt) selected from the group consisting of p-toluenesulfonic acid, methanesulfonic acid, ethanesulfonic acid, benzenesulfonic acid, naphthalenesulfonic acid and aluminum sulfate.

Examples of hexitols that can be used in the preparation method of the present invention include sorbitol, mannitol, and iditol. Among these, sorbitol which can be easily prepared through hydrogenation of starch-derived glucose is most preferably used.

The first acid of the mixed acid used in the dehydration reaction is sulfuric acid, and the second acid is at least one selected from p-toluenesulfonic acid, methanesulfonic acid, ethanesulfonic acid, benzenesulfonic acid, naphthalenesulfonic acid and aluminum sulfate.

A lower amount of a mixed acid catalyst added in terms of process efficiency leads to higher conversion rate and economic efficiency. The amount of the mixed acid added in the present invention is in the range of 0.5 to 10 parts by weight based on 100 parts by weight of hexitol, preferably 0.5 to 5 parts by weight, and more preferably 0.5 to 3 parts by weight. If the amount of the mixed acid is lower than 0.5 parts by weight, dehydration time is disadvantageously too long. On the other hand, if the amount of the mixed acid is higher than 10 parts by weight, there are problems associated with large production of saccharide polymers as a by-product and lowering of a conversion rate.

The first acid and the second acid used may be ones of commonly used concentrations, and can also be appropriately selected and used by a person skilled in the art depending on the object and disclosed details of the present invention. Several acid concentrations are exemplified in the following examples.

The ratio of first acid to the second acid in the mixed acid may be in a range of 1:9 to 7:3 by weight ratio. If the ratio is lower than 1:9, this results in lowering of anhydrosugar alcohol production. On the other hand, if the ratio is higher than 7:3, the production of saccharide polymers is disadvantageously increased due to excess sulfuric acid.

The dehydration reaction is carried out by adding a mixed acid to hexitol. The reaction is preferably carried out at a temperature of 105 to 190° C. for 1 to 10 hours under vacuum conditions of 5 mmHg or less.

Examples of the anhydrosugar alcohol prepared by the preparation method of the present invention include isosorbide, isomannide and isoidide.

In accordance with another aspect of the present invention, there is provided a method for the preparation of an anhydrosugar alcohol, including dehydrating hexitol with a mixed acid of first acid and second acid to produce an anhydrosugar alcohol and purifying the resulting anhydrosugar alcohol, wherein the first acid is sulfuric acid, and the second acid is at least one sulfur-containing acid (sulfur-containing acid salt) selected from the group consisting of p-toluenesulfonic acid, methanesulfonic acid, ethanesulfonic acid, benzenesulfonic acid, naphthalenesulfonic acid and aluminum sulfate.

Details of hexitol, mixed acid, dehydration reaction and anhydrosugar alcohol have been described above.

The above-described purification may be carried out by distillation or the like at a temperature of preferably 150 to 250° C. under vacuum conditions of 5 mmHg or less. If the distillation temperature is lower than 150° C., distillation of anhydrosugar alcohol is not readily carried out. On the other hand, if the distillation temperature is higher than 250° C., this results in a dark color of anhydrosugar alcohol, thus presenting difficulty of decoloration. The distillation may be carried out using a conventional condenser or thin-film evaporator.

If necessary, the distillate obtained by distillation may also be further treated with activated carbon/activated clay for the purpose of decoloration. Further, if necessary, prior to carrying out distillation, the temperature of the dehydration product may be lowered to a range of 60 to 120° C., followed by neutralization through addition of an alkali such as sodium hydroxide, calcium hydroxide or ammonium hydroxide.

The preparation method of the present invention enables the preparation of an anhydrosugar alcohol with an improved purification yield of 65% or higher while achieving an increased conversion rate of 80% or higher.

Advantageous Effects of Invention

The method for the preparation of an anhydrosugar alcohol in accordance with the present invention enables the production of an anhydrosugar alcohol with high conversion rate and purification yield within a short period of time, using simple facilities and a low-priced acid catalyst (mixed acid).

In particular, the method for the preparation of an anhydrosugar alcohol in accordance with the present invention extends applicability of starches by using starch-derived hexitol which is a principal raw material of environmentally-friendly green industry as biomass.

Anhydrosugar alcohol produced by the preparation method of the present invention is useful as an industrial raw material which may be utilized in heat-resistant PET, polyester fibers, high-strength sheets, films, polyurethanes, etc.

MODE FOR THE INVENTION

Now, the present invention will be described in more detail with reference to the following examples. These examples are provided only to illustrate the present invention and should not be construed as limiting the scope and spirit of the present invention.

EXAMPLES

Determination of Efficiency

Analysis of conversion rate and purity of the prepared anhydrosugar alcohol was carried out using a gas chromatograph (GC) (HP5890).

Conversion rate: (moles of anhydrosugar alcohol produced/moles of hexitol input)×100

Yield: (moles of anhydrosugar alcohol after purification and decoloration/moles of hexitol input)×100

Example 1

1,000 g of a sorbitol powder (D-sorbitol, Samyang Genex Corp., Korea) was introduced into a three-necked glass reactor equipped with a stirrer and dissolved by elevating a temperature of the reactor to 110° C. under vacuum conditions of 3 mmHg. A mixed acid of 5 g of concentrated sulfuric acid (95%, Duksan Chemical Engineering, Co., Ltd., Korea) and 10 g of methanesulfonic acid (70%, Sigma) was added thereto, and then the reaction temperature was elevated to 145° C. The dehydration reaction was carried out for 3 hours under vacuum, resulting in conversion of sorbitol into isosorbide which is an anhydrosugar alcohol. The temperature of the reactor was lowered to 110° C., and 20 g of a 50% sodium hydroxide solution (Samchun Pure Chemical Co., Ltd., Korea) was added to neutralize the dehydration reaction liquid. Here, the anhydrosugar alcohol conversion rate was 85.4%, and the content of the resulting polymer was 6.3%.

The neutralized anhydrosugar alcohol liquid was distillated under 3 mmHg vacuum while elevating the temperature thereof to 190° C. To the resulting distillate was added distilled water, thus preparing a 40% solution. Activated carbon was added thereto for decoloration, followed by concentration to produce an anhydrosugar alcohol (isosorbide) with a solid content of 85%. Purity of the anhydrosugar alcohol (calculated in terms of an amount of isosorbide in the total amount of solids by GC analysis of the converted solution) was 99.2%, and the total yield was 67.3%.

Example 2

The procedure was carried out in the same manner as in Example 1, except that 10 g of sulfuric acid and 10 g of methanesulfonic acid were used as a mixed acid, and 30 g of sodium hydroxide solution was used for neutralization. The conversion rate was 91.2%, and the amount of the resulting polymer was 4.8%. After carrying out purification, yield and purity were 72.1% and 99.7%, respectively.

Example 3

The procedure was carried out in the same manner as in Example 1, except that 15 g of sulfuric acid and 15 g of methanesulfonic acid were used as a mixed acid, the dehydration reaction temperature was 130° C., and 50 g of sodium hydroxide solution was used for neutralization. The conversion rate was 94.5%, and the amount of the resulting polymer was 3.6%. After purification, yield and purity were 76.1% and 99.7%, respectively.

Example 4

The procedure was carried out in the same manner as in Example 1, except that 10 g of sulfuric acid and 10 g of aluminum sulfate (99%, Daejung Chemicals & Metals Co., Ltd., Korea) were used as a mixed acid, and 30 g of sodium hydroxide solution was used for neutralization. The conversion rate was 90.2%, and the amount of the resulting polymer was 5.7%. After carrying out purification, yield and purity were 66.9% and 99.3%, respectively.

Example 5

The procedure was carried out in the same manner as in Example 1, except that 10 g of sulfuric acid and 15 g of aluminum sulfate were used as a mixed acid, and 35 g of sodium hydroxide solution was used for neutralization. The conversion rate was 91.2%, and the amount of the resulting polymer was 4.9%. After carrying out purification, yield and purity were 68.4% and 99.3%, respectively.

Example 6

The procedure was carried out in the same manner as in Example 1, except that 10 g of sulfuric acid and 15 g of p-toluenesulfonic acid (99%) were used as a mixed acid, the dehydration reaction temperature was 150° C., and 35 g of sodium hydroxide solution was used for neutralization. The conversion rate was 88.1%, and the amount of the resulting polymer was 5.3%. After carrying out purification, yield and purity were 70.6% and 99.3%, respectively.

Comparative Example 1

The procedure was carried out in the same manner as in Example 1, except that 20 g of sulfuric acid was used as a dehydration catalyst. The conversion rate was 87.7%, and the amount of the resulting polymer was 9.6%. After carrying out purification, yield and purity were 48.2% and 98.5%, respectively.

Comparative Example 2

The procedure was carried out in the same manner as in Example 1, except that 30 g of methanesulfonic acid was used as a dehydration catalyst. The conversion rate was 79.3%, and the amount of the resulting polymer was 8.2%. After carrying out purification, yield and purity were 56.2% and 99.1%, respectively.

Comparative Example 3

The procedure was carried out in the same manner as in Example 1, except that 20 g of aluminum sulfate was used as a dehydration catalyst. The conversion rate was 66.5%, and the amount of the resulting polymer was 6.9%. After carrying out purification, yield and purity were 51.2% and 99.0%, respectively.

Comparative Example 4

The procedure was carried out in the same manner as in Example 1, except that 10 g of sulfuric acid and 10 g of phosphoric acid (99%) were used as a dehydration catalyst. The conversion rate was 64.0%, and the amount of the resulting polymer was 7.7%. After carrying out purification, yield and purity were 48.5% and 98.2%, respectively.

TABLE 1

| | Catalyst (parts by weight based on 100 parts by weight of hexitol) | Conversion rate (%) | Polymer (wt %) | Yield (%) |
|---|---|---|---|---|
| Example 1 | Sulfuric acid 0.5 Methanesulfonic acid 1.0 | 85.4 | 6.3 | 67.3 |
| Example 2 | Sulfuric acid 1.0 Methanesulfonic acid 1.0 | 91.2 | 4.8 | 72.1 |
| Example 3 | Sulfuric acid 1.5 Methanesulfonic acid 1.5 | 94.5 | 3.6 | 76.1 |
| Example 4 | Sulfuric acid 1.0 Aluminum sulfate 1.0 | 90.2 | 5.7 | 66.9 |
| Example 5 | Sulfuric acid 1.0 Aluminum sulfate 1.5 | 91.2 | 4.9 | 68.4 |
| Example 6 | Sulfuric acid 1.0 p-toluenesulfonic acid 1.5 | 88.1 | 5.3 | 70.6 |
| Comparative Example 1 | Sulfuric acid 2.0 | 87.7 | 9.6 | 48.2 |
| Comparative Example 2 | Methanesulfonic acid 3.0 | 79.3 | 8.2 | 56.2 |
| Comparative Example 3 | Aluminum sulfate 2.0 | 66.5 | 6.9 | 51.2 |
| Comparative Example 4 | Sulfuric acid 1.0 Phosphoric acid 1.0 | 64.0 | 7.7 | 48.5 |

<Conversion Rate, Polymer Productivity and Yield>

As can be seen from Table 1 above, it was demonstrated that the preparation method of the present invention using a mixed acid as a dehydration catalyst of hexitol (Examples 1 to 6) exhibits high conversion rate and yield and low production of polymer by-products.

Although the preferred embodiments of the present invention have been disclosed for illustrative purposes, those skilled in the art will appreciate that various modifications, additions and substitutions are possible, without departing from the scope and spirit of the invention as disclosed in the accompanying claims.

The invention claimed is:

1. A method for the preparation of an anhydrosugar alcohol, comprising dehydrating hexitol with a mixed acid of first acid and second acid, wherein the first acid is sulfuric acid, and the second acid is at least one sulfur-containing acid or sulfur-containing acid salt selected from the group consisting of p-toluenesulfonic acid, methanesulfonic acid, ethanesulfonic acid, benzenesulfonic acid, naphthalenesulfonic acid and aluminum sulfate.

2. A method for the preparation of an anhydrosugar alcohol, comprising dehydrating hexitol with a mixed acid of first acid and second acid to produce an anhydrosugar alcohol and purifying the anhydrosugar alcohol, wherein the first acid is sulfuric acid, and the second acid is at least one sulfur-containing acid or sulfur-containing acid salt selected from the group consisting of p-toluenesulfonic acid, methanesulfonic acid, ethanesulfonic acid, benzenesulfonic acid, naphthalenesulfonic acid and aluminum sulfate.

3. The method according to claim 1, wherein the mixed acid is added in an amount of 0.5 to 10 parts by weight based on 100 parts by weight of hexitol.

4. The method according to claim 1, wherein the ratio of first acid to second acid in the mixed acid is in the range of 1:9 to 7:3 by weight.

5. The method according to claim 1, wherein the hexitol is at least one selected from the group consisting of sorbitol, mannitol and iditol.

6. The method according to claim 1, wherein the dehydration reaction is carried out at a temperature of 105 to 190° C. for 1 to 10 hours under vacuum.

7. The method according to claim 2, wherein the purification is carried out by vacuum distillation at a temperature of 150 to 250° C.

8. The method according to claim 7, further comprising an activated carbon or activated clay treatment step for decoloration.

9. The method according to claim 7, further comprising, prior to carrying out distillation, adding an alkali to neutralize the dehydration product.

10. The method according to claim 1, wherein the anhydrosugar alcohol is at least one selected from the group consisting of isosorbide, isomannide and isoidide.

11. The method according to claim 2, wherein the mixed acid is added in an amount of 0.5 to 10 parts by weight based on 100 parts by weight of hexitol.

12. The method according to claim 2, wherein the ratio of first acid to second acid in the mixed acid is in the range of 1:9 to 7:3 by weight.

13. The method according to claim 2, wherein the hexitol is at least one selected from the group consisting of sorbitol, mannitol and iditol.

14. The method according to claim 2, wherein the dehydration reaction is carried out at a temperature of 105 to 190° C. for 1 to 10 hours under vacuum.

15. The method according to claim 2, wherein the anhydrosugar alcohol is at least one selected from the group consisting of isosorbide, isomannide and isoidide.

* * * * *